US012740965B2

(12) United States Patent
Hohendanner et al.

(10) Patent No.: US 12,740,965 B2
(45) Date of Patent: Sep. 22, 2026

(54) SOTAGLIFLOZIN FOR IMPROVING LEFT ATRIAL FUNCTION

(71) Applicant: Lexicon Pharmaceuticals, Inc., The Woodlands, TX (US)

(72) Inventors: Felix Hohendanner, Berlin (DE); Frank Heinzel, Berlin (DE)

(73) Assignee: LEXICON PHARMACEUTICALS, INC., The Woodlands, TX (US)

(*) Notice: Subject to any disclaimer, the term of this patent is extended or adjusted under 35 U.S.C. 154(b) by 431 days.

(21) Appl. No.: 18/270,598

(22) PCT Filed: Jan. 4, 2022

(86) PCT No.: PCT/EP2022/050087

§ 371 (c)(1),
(2) Date: Jun. 30, 2023

(87) PCT Pub. No.: WO2022/144465

PCT Pub. Date: Jul. 7, 2022

(65) Prior Publication Data

US 2024/0100013 A1 Mar. 28, 2024

Related U.S. Application Data

(60) Provisional application No. 63/134,792, filed on Jan. 7, 2021, provisional application No. 63/133,662, filed on Jan. 4, 2021.

(51) Int. Cl.
*A61K 31/351* (2006.01)
*A61P 9/00* (2006.01)

(52) U.S. Cl.
CPC .............. *A61K 31/351* (2013.01); *A61P 9/00* (2018.01)

(58) Field of Classification Search
CPC ................................ A61K 31/351; A61P 9/00
USPC .......................................................... 514/460
See application file for complete search history.

(56) References Cited

U.S. PATENT DOCUMENTS

| | | | |
|---|---|---|---|
| 7,781,577 B2 | 8/2010 | Harrison et al. | |
| 7,846,945 B2 | 12/2010 | Harrison et al. | |
| 8,476,413 B2 | 7/2013 | Harrison et al. | |
| 9,365,602 B2 | 6/2016 | Harrison et al. | |
| 2022/0370485 A1* | 11/2022 | Bhatt | A61P 9/04 |

FOREIGN PATENT DOCUMENTS

WO 2021037400 A1 3/2021

OTHER PUBLICATIONS

Bhatt et al New England Journal of Medicine, 2021, 384, 117-128 (Year: 2021).*
Al-Abdouh, A , et al., “A Meta-Analysis of the Sodium-Glucose Cotransporter 2 Inhibitors in Patients With Heart Failure and Preserved Ejection Fraction”, American Journal of Cardiology 164, 138-141 (2021).
Bhatt, D , et al., “Sotagliflozin in Patients with Diabetes and Recent Worsening Heart Failure”, N Engl J Med 384 (2), 117- 128 (2020).
Bode, D , et al., “Dual SGLT-1 and SGLT-2 inhibition improves left atrial dysfunction in HFpEF”, Cardiovascular Diabetology 20, 14 pages (2021).
Goette, A , et al., “EHRA/HRS/APHRS/SOLAECE expert consensus on Atrial cardiomyopathies: Definition, characterisation, and clinical implication”, J Arrhythm 32 (4), 247-278 (2016).
Patent Cooperation Treaty , International Search Report and Written Opinion for PCT/EP2022/050087, 11 pages, dated May 4, 2022.
Soga, F , et al., “Impact of dapagliflozin on left ventricular diastolic function of patients with type 2 diabetic mellitus with chronic heart failure”, Cardiovasc Diabetol 17, 132, (2018).
Washburn, W , et al., “Evolution of sodium glucose co-transporter 2 inhibitors as anti-diabetic agents”, Expert Opin Ther Patents 19 (11), 1485-1499 (2009).

* cited by examiner

*Primary Examiner* — Yevgeny Valenrod
(74) *Attorney, Agent, or Firm* — VIKSNINS HARRIS PADYS MALEN LLP

(57) ABSTRACT

This invention relates to sotagliflozin for use in methods of improving left atrial function, of treating and/or preventing atrial cardiomyopathy, and treating and/or preventing atrial fibrillation, and to compounds and pharmaceutical compositions useful therein.

4 Claims, 12 Drawing Sheets

A

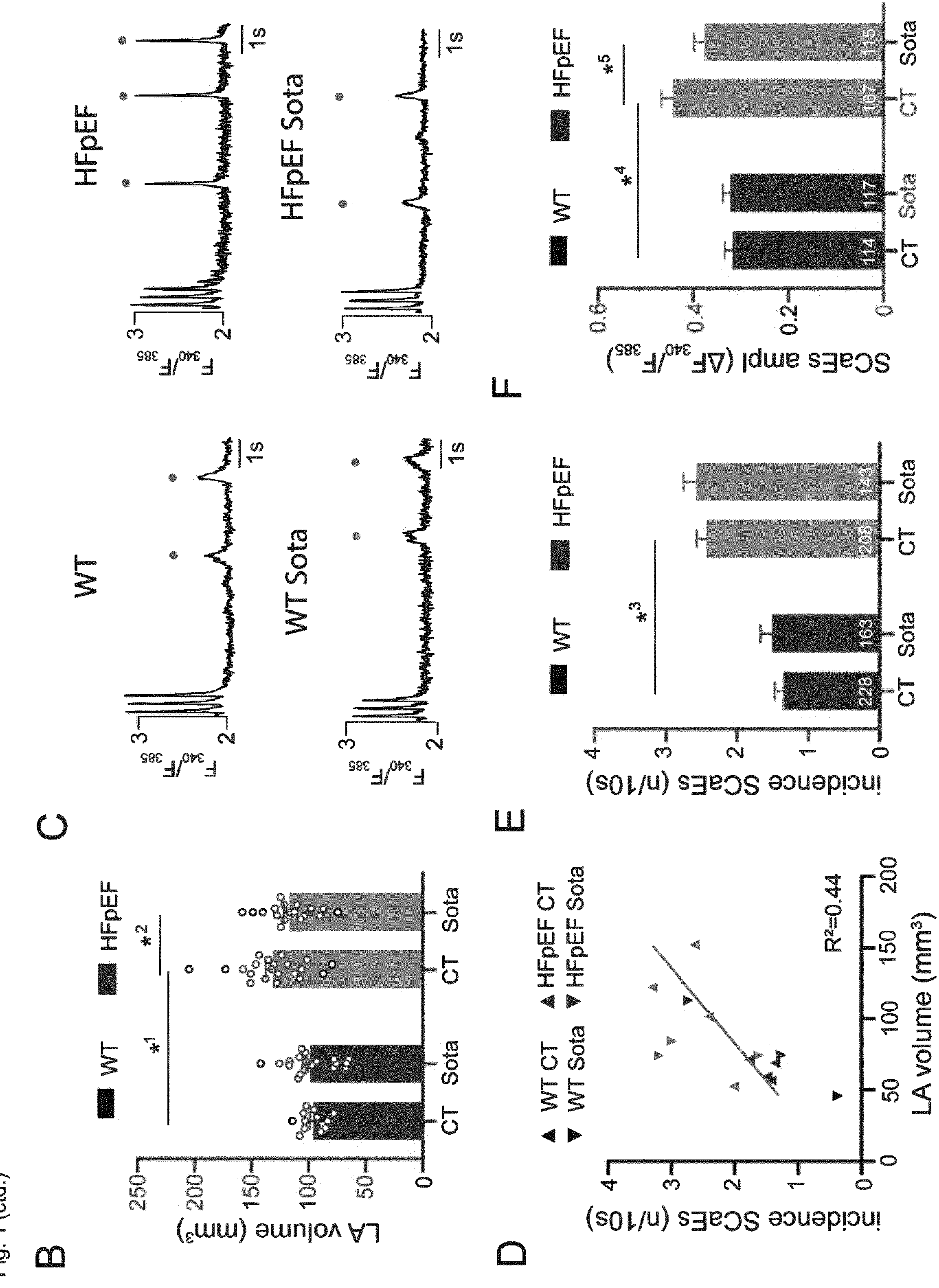
Fig. 1 (ctd.)
B
WT
HFpEF
LA volume (mm³)
*1
*2
CT Sota CT Sota
C
WT
WT Sota
HFpEF
HFpEF Sota
F340/F385
1s
D
WT CT
WT Sota
HFpEF CT
HFpEF Sota
incidence SCaEs (n/10s)
LA volume (mm³)
R²=0.44
E
incidence SCaEs (n/10s)
*3
228 163 208 143
CT Sota CT Sota
F
SCaEs ampl (ΔF340/F385)
*4
*5
114 117 167 115
CT Sota CT Sota A
B
C
D
E
F
1 Hz, 2 mM Ca2+
WT CT
HFpEF CT
WT Sota
HFpEF Sota
F340/F385
time (s)
3 Hz, 5 mM Ca2+
WT
HFpEF
n.s.
diast. Ca2+ (F340/F385) 1 Hz
CaT ampl. (ΔF340/F385) 1 Hz
diast. Ca2+ (F340/F385) 3 Hz
CaT ampl. (ΔF340/F385) 3 Hz
CT
Sota
129
112
89
77
*2
*1

G
WT
HFpEF
time-to-peak (ms) 3 Hz
n.s.
129
112
89
77
CT Sota CT Sota
H
mannitol
glucose
1 min
WT
WT Sota
HFpEF
HFpEF Sota
F340/F385
1s
I
WT CT
WT Sota
HFpEF CT
HFpEF Sota
*3
*4
*5
diast. Ca2+ (F340/F385)
man glc man glc man glc man glc
J
WT
HFpEF
*6
Δ diast. Ca2+ (ΔF340/F385)
CT Sota CT Sota

D

E

F

B

A
ROS (H2-DCF)
t = 0 s
t = 15 s
t = 90 s
10 µm
B
HFpEF
HFpEF Sota
glucose
1ΔF/F0
10 s
C
HFpEF
HFpEF Sota
ROS production (ΔF/(F0*ms))
man
glc
D
mitochondrial fission (a.u.)
E
WT
WT Sota
glucose
2DG
3 min
1s F
WT CT
WT Sota
HFpEF CT
HFpEF Sota
diast. Ca2+ (F340/F385)
1
0.8
0.6
0.4
*4
glc
2DG
G
WT
HFpEF
Δ diast. Ca2+ (ΔF340/F385)
0.2
0.1
0
-0.1
-0.2
*5
*6
CT
Sota
H
CaT ampl. (ΔF340/F385)
1.5
1
0.5
0
*7
I
Δ CaT ampl. (ΔF340/F385)
0.6
0.4
0.2
-0.2
-0.4
*8
*9

SOTAGLIFLOZIN FOR IMPROVING LEFT ATRIAL FUNCTION

This application claims the right of priority of U.S. Provisional Patent Applications U.S. 63/133,662 (filed 4, Jan. 2021) and U.S. 63/134,792 (filed 7, Jan. 2021), both incorporated by reference herein.

FIELD

This invention relates to sotagliflozin for use in treatment of deficiency of heart function, particularly in improving left atrial function, or treating and/or preventing atrial cardiomyopathy, and treating and/or preventing atrial fibrillation. The invention similarly relates to methods of improving left atrial function, of treating and/or preventing atrial cardiomyopathy, and treating and/or preventing atrial fibrillation (e.g., in a patient suffering from heart failure with preserved ejection fraction), and to compounds and pharmaceutical compositions useful therein.

BACKGROUND

Atrial cardiomyopathy is a complex of structural, architectural, contractile, or electrophysiological changes affecting the atria with the potential to produce clinically relevant manifestations. Goette, A. et al, J Arrhythm. 2016 August; 32(4): 247-278. Many diseases (e.g., hypertension, heart failure, diabetes, and myocarditis) and conditions (e.g., ageing, endocrine abnormalities) are known to induce or contribute to atrial cardiomyopathy. Often characterized by atrial enlargement (with or without atrial fibrillation), it can be found in patients suffering from heart failure (HF) with preserved ejection fraction (HFpEF), heart failure with reduced ejection fraction (HFrEF), valvular disease, and other cardiac conditions.

Heart failure (e.g., HFpEF) is an increasingly prevalent disease. Left atrial (LA) cardiomyopathy and remodeling are hallmark features of HFpEF and commonly associated with LA enlargement and (precursors of) atrial fibrillation. Catheter ablation, rather than medical therapy (rate/rhythm control), is currently the most effective treatment for AF to reduce mortality and heart failure hospitalization in patients with HF with reduced ejection fraction. A need exists for other methods of treatment and of improving left atrial function in general.

The sodium-glucose cotransporter 2 (SGLT2) is one of 14 transmembrane-domain SGLTs and is responsible for reabsorbing most of the glucose filtered at the glomerulus, and several SGLT2 inhibitors are now used to treat type 2 diabetes. Most pharmaceutical efforts directed at discovering and developing inhibitors of SGLT2 "have focused on devising inhibitors selective for the SGLT2 transporter." Washburn, W. N., Expert Opin. Ther. Patents 19(11):1485, 1499, 1486 (2009). This is apparently based, at least in part, on the fact that while humans lacking a functional SGLT2 gene appear to live normal lives—apart from exhibiting high urinary glucose excretion—those bearing a SGLT1 gene mutation experience glucose-galactose malsorption. Id. Unlike SGLT2, which is expressed exclusively in the human kidney, SGLT1 is also expressed in the small intestine and heart. Id.

Unlike sodium-glucose cotransporter inhibitors currently marketed for the treatment of diabetes, the compound sotagliflozin inhibits both SGLT1 and SGLT2. While sotagliflozin has been approved in Europe for the treatment of type 1 diabetes, its effectiveness in the treatment of other diseases and disorders remains unknown.

Based on the above-mentioned state of the art, the objective of the present invention is to provide means and methods to improve left atrial function and to facilitate treatment or prevention of atrial cardiomyopathy, and/or atrial fibrillation.

This objective is attained by the subject-matter of the independent claims of the present specification, with further advantageous embodiments described in the dependent claims, examples, figures and general description of this specification.

SUMMARY OF THE INVENTION

The present invention is directed, in one aspect, to methods of improving left atrial function. It is also directed to methods of treating and/or preventing atrial cardiomyopathy, as well as to methods of treating and/or preventing atrial fibrillation (e.g., in a patient suffering from heart failure with preserved ejection fraction (HFpEF)). Particular methods comprise the administration of a therapeutically or prophylactically effective amount of sotagliflozin.

Terms and Definitions

Some abbreviations used herein are defined below:

AF atrial fibrillation
CaT $Ca^{2+}$ transient
EF ejection fraction
HF heart failure
HFpEF heart failure with preserved ejection fraction
HFrEF heart failure with reduced ejection fraction
LA left atrium/left atrial
NCX sodium-glucose exchanger
ROS reactive oxygen species
SCaE sarcoplasmic reticulum $Ca^{2+}$ release events
SGLT sodium-glucose linked transporter
Sota sotagliflozin
SR sarcoplasmic reticulum
T2DM diabetes mellitus type 2
WT wild type For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "comprising," "having," "containing," and "including," and other similar forms, and grammatical equivalents thereof, as used herein, are intended to be equivalent in meaning and to be open-ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Thus, unless otherwise indicated, the term "include" has the same meaning as "include, but are not limited to," and the term "includes" has the same meaning as "includes but is not limited to." Similarly, the term "such as" has the same meaning as the term "such as, but not limited to."

Where a range of values is provided, it is understood that each intervening value, to the tenth of the unit of the lower limit, unless the context clearly dictates otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic, and biochemical methods (see generally, Sambrook et al., Molecular Cloning: A Laboratory Manual, 4th ed. (2012) Cold Spring Harbor Laboratory Press, Cold Spring Harbor, N.Y. and Ausubel et al., Short Protocols in Molecular Biology (2002) 5th Ed, John Wiley & Sons, Inc.) and chemical methods.

The term metabolic syndrome refers to occurrence of at least three of the following five medical conditions in a patient: abdominal obesity, high blood pressure, high blood sugar, high serum triglycerides, and low serum high-density lipoprotein (HDL).

The International Diabetes Federation consensus worldwide definition of metabolic syndrome (2006) is: Central obesity (defined as waist circumference with ethnicity-specific values) AND any two of the following:

- Raised triglycerides: >150 mg/dL (1.7 mmol/L), or specific treatment for this lipid abnormality
- Reduced HDL cholesterol: <40 mg/dL (1.03 mmol/L) in males, <50 mg/dL (1.29 mmol/L) in females, or specific treatment for this lipid abnormality
- Raised blood pressure (BP): systolic BP>130 or diastolic BP>85 mm Hg, or treatment of previously diagnosed hypertension
- Raised fasting plasma glucose (FPG): >100 mg/dL (5.6 mmol/L), or previously diagnosed type 2 diabetes If FPG is >5.6 mmol/L or 100 mg/dL, an oral glucose tolerance test is strongly recommended, but is not necessary to define presence of the syndrome.

If BMI is >30 kg/m2, central obesity can be assumed and waist circumference does not need to be measured. Source: Wikipedia.

According to Ning et al. (Front. Cardiovasc. Med., 9 Aug. 2021|https://doi.org/10.3389/fcvm.2021.674612), expert consensus defines the term atrial cardiomyopathy as "any complex of structural, architectural, contractile, or electrophysiological changes affecting the atria with the potential to produce clinically relevant manifestations" (Goette et al. EHRA/HRS/APHRS/SOLAECE expert consensus on atrial cardiomyopathies: definition, characterization, and clinical implication. Europace. (2016) 18:1455-90. doi: 10.1093/europace/euw161). Meanwhile, atrial cardiomyopathy was proposed (Kamel et al., Future Cardiol. (2015) 11:323-31. doi: 10.2217/fca.15.22) as a term to describe patients with abnormal atrial substrate and function, including atrial fibrosis, atrial mechanical dysfunction, atrial electrical dysfunction, and hypercoagulable state, which can be present even without atrial fibrillation (AF).

The term atrial fibrillation (AF or A-fib) in the context of the present specification relates to an abnormal heart rhythm (arrhythmia) characterized by rapid and irregular beating of the atrial chambers of the heart. AF encompasses short periods of abnormal beating, which may become longer or continuous as the clinical manifestation progresses. It may also start as other forms of arrhythmia such as atrial flutter that then transform into AF. Episodes can be asymptomatic. Symptomatic episodes may involve heart palpitations, fainting, lightheadedness, shortness of breath, or chest pain.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A "prophylactically effective amount" of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

DETAILED DESCRIPTION OF THE INVENTION

This invention is based, in part, in vivo studies of the compound sotagliflozin (CAS No 1018899-04-1), a dual SGLT1/2 inhibitor chemically named (2S,3R,4R,5S,6R)-2-(4-chloro-3-(4-ethoxybenzyl)phenyl)-6-(methylthio)tetrahydro-2H-pyran-3,4,5-triol and having the structure:

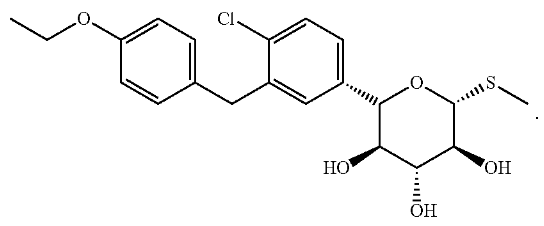

Solid forms of sotagliflozin have been disclosed. See, e.g., U.S. Pat. No. 8,217,156. Oral solid dosage forms of the compound have also been disclosed. See, e.g., U.S. patent application publication no. US-2012-0172320-A1.

2nd Medical Indication

In one aspect, the invention relates to sotagliflozin for use in treatment or prevention of atrial cardiomyopathy. One surrogate parameter of atrial cardiomyopathy is atrial enlargement. Sotagliflozin has been observed to decrease pathological left atrial enlargement. The indication might consequently also be rephrased as the use to treat or prevent left atrial enlargement.

In an alternative of this aspect of the invention, sotagliflozin is provided for use in treatment or prevention of atrial fibrillation.

In another alternative of this aspect of the invention, sotagliflozin is provided for use in treatment or prevention of supraventricular tachycardia, particularly for use in treatment or prevention of atrial tachycardia.

In certain embodiments, sotagliflozin is provided for administration to a patient diagnosed with heart failure with preserved ejection fraction (HFpEF).

In certain embodiments, sotagliflozin is provided for administration to a patient who has been diagnosed with metabolic syndrome. Of note, the examples include data obtained in animals useful as a model for metabolic syndrome. The inventors have observed that the drug improves mitochondrial calcium intake. Mitochondrial energy metabolism is affected in patients with metabolic syndrome, and improving calcium intake is expected to contribute to an improvement of clinical parameters in these patients.

In certain embodiments, sotagliflozin is administered orally, particularly administered at a dose of at least 200 mg (particularly 250, 300, 350, or 400 mg) per day.

Medical Treatment

This invention encompasses methods of improving left atrial function, of treating and/or preventing atrial cardiomyopathy, and treating and/or preventing atrial fibrillation. Particular methods comprise treating a patient suffering from HFpEF. Particular methods comprise the administration of a therapeutically or prophylactically effective amount of sotagliflozin (e.g., at least 200 mg per day). In preferred methods, the sotagliflozin is orally administered.

One embodiment of this invention encompasses a method of improving left atrial function in a patient in need thereof, which comprises administering to the patient a therapeutically or prophylactically effective amount of sotagliflozin. In a particular method, the patient is suffering from heart failure with preserved ejection fraction (HFpEF).

Another embodiment of this invention encompasses a method of treating and/or preventing atrial cardiomyopathy in a patient in need thereof, which comprises administering to the patient a therapeutically or prophylactically effective amount of sotagliflozin. In a particular method, the patient is suffering from heart failure with preserved ejection fraction (HFpEF).

Another embodiment of this invention encompasses a method of treating and/or preventing atrial fibrillation in a patient in need thereof, which comprises administering to the patient a therapeutically or prophylactically effective amount of sotagliflozin. In a particular method, the patient is suffering from heart failure with preserved ejection fraction (HFpEF).

In certain embodiments of this invention, the therapeutically or prophylactically effective amount of sotagliflozin is administered orally. In certain embodiments of this invention, the therapeutically or prophylactically effective amount of sotagliflozin is at least 200 mg (e.g., 200, 250, 300, 350, or 400 mg) per day.

Pharmaceutical Compositions, Administration/Dosage Forms and Salts

Similarly, an orally administratable dosage form for the prevention or treatment of improving left atrial function, treatment or prevention of atrial cardiomyopathy, and/or treatment or prevention of atrial fibrillation is provided, the dosage form comprising sotagliflozin.

The invention further encompasses a pharmaceutical composition comprising a compound of the present invention, or a pharmaceutically acceptable salt thereof, and a pharmaceutically acceptable carrier. In further embodiments, the composition comprises at least two pharmaceutically acceptable carriers, such as those described herein.

Method of Manufacture and Method of Treatment According to the Invention

The invention further encompasses, as an additional aspect, the use of for use in a method of manufacture of a medicament for the prevention or treatment of improving left atrial function, for the treatment or prevention of atrial cardiomyopathy, and/or for treatment or prevention of atrial fibrillation, as laid out above in any of the aspects and embodiments of the invention.

Wherever alternatives for single separable features are laid out herein as "embodiments", it is to be understood that such alternatives may be combined freely to form discrete embodiments of the invention disclosed herein. Thus, any of the alternative dosage amounts given herein may be combined with any of the medical indications method mentioned herein.

The invention is further illustrated by the following examples and figures, from which further embodiments and advantages can be drawn. These examples are meant to illustrate the invention but not to limit its scope.

BRIEF DESCRIPTION OF THE FIGURES

Aspects of this invention may be understood with reference to the attached figures, briefly described below.

EXAMPLES

Figure 1:
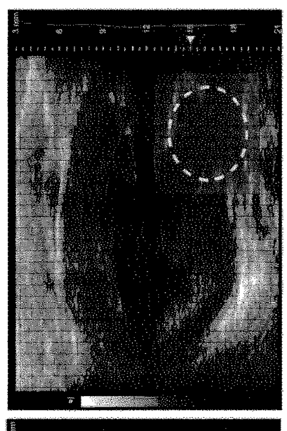
FIG. 1. (A) Representative B-mode images in parasternal long axis view. Dashed circles indicate the LA. (B) Related data of LA volume. (C) Representative recordings of spontaneous $Ca^{2+}$ release during a non-stimulated interval, following stimulation at 3 Hz for 10 s. (D) Linear regression of arrhythmic SR $Ca^{2+}$ release events (SCaEs) in-vitro (average per animal) and LA volume in vivo. (E) Occurrence of SCaEs and their (F) corresponding CaT amplitude (average per cell, respectively). Statistical analysis: Two-way ANOVA followed by post-hoc Bonferroni. p-values: [1]0.001, [2]0.045, [3]<0.001, [4]0.028, [5]<0.001. (B) n=animals, (E, F) n=cells derived from 6 animals per group.
Figure 1:
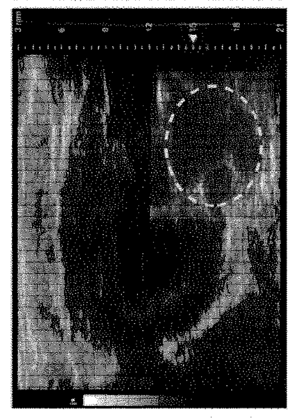
Figure 1:
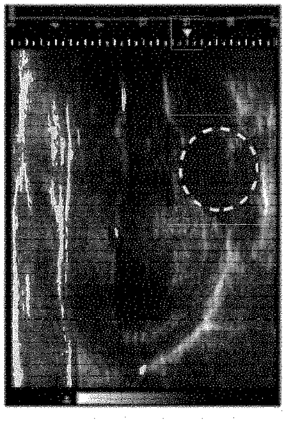
Figure 1:
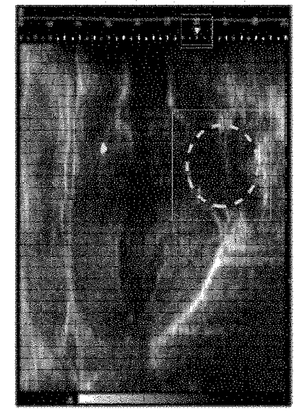

The invention is based on discoveries made by studying chronic treatment with sotagliflozin on left atrial (LA) remodeling and cellular arrhythmogenesis (i.e., atrial cardiomyopathy) in a metabolic syndrome-related rat model of HFpEF. The model and methods used are described below.

Materials and Methods

Heart Failure Model

Animal experiments were approved by local authorities. The ZSF-1 obese rat model is based on a leptin receptor mutation resulting in severe metabolic dysfunction. See Bilan V P, Salah E M, Bastacky S, Jones H B, Mayers R M, Zinker B, Poucher S M, Tofovic S P: "Diabetic nephropathy and long-term treatment effects of rosiglitazone and enalapril in obese ZSF1 rats," *J Endocrinol* 2011, 210(3):293-308. The model has repeatedly been reported to show distinct features of HFpEF, such as an increased left ventricular (LV) end diastolic pressure, LV hypertrophy, diastolic dysfunction, lung congestion and LA remodeling, while maintaining a preserved ejection fraction (EF). See, e.g., Bowen T S, Brauer D, Rolim N P L, Baekkerud F H, Kricke A, Ormbostad Berre A M, Fischer T, Linke A, da Silva G J, Wisloff U et al: "Exercise Training Reveals Inflexibility of the Diaphragm in an Animal Model of Patients with Obesity-Driven Heart Failure with a Preserved Ejection Fraction," *Journal of the American Heart Association* 2017, 6(10). Wild-type (WT) rats (Wistar Kyoto and HFpEF (ZSF-1 obese) animals were obtained at ten weeks (Charles River Laboratories, MA, USA) and fed a high caloric diet (Purina 5008; LabDiet, MO, USA). At 16 weeks, animals were randomly assigned to receive treatment (oral feeding) with either vehicle or the dual SGLT1/2 inhibitor sotagliflozin (30 mg/kg/day; reported to exhibit near maximal urinary glucose secretion in rats for seven weeks until final experiments were performed.

Serum biomarkers. Serum biomarkers were assessed by a licensed laboratory for veterinary diagnostics (Institut für veterinarmedizinische Diagnostik, Germany) using validated photometric (β-hydroxybutyrate) and enzymatic (creatinine, urea) assays.

Echocardiography. Echocardiography was performed and analyzed as previously described (See Hohendanner F, Bode D, Primessnig U, Guthof T, Doerr R, Jeuthe S, Reimers S, Zhang K, Bach D, Wakula P et al: "Cellular mechanisms of metabolic syndrome-related atrial decompensation in a rat model of HFpEF" *J Mol Cell Cardiol* 2018, 115:10-19) by an experienced observer (N.H.) blinded to the treatment group immediately prior to sacrifice using a vevo lab ultrasound system to assess LA size and LV fractional shortening in vivo. 1-lead electrocardiograms were obtained during echocardiography and the presence or absence of atrial rhythm disorders i.e., atrial fibrillation was documented.

Cardiomyocyte isolation. LA and LV cardiomyocytes were isolated using enzymatic digestion as previously described in detail. See Bode D, Guthof T, Pieske B M, Heinzel F R, Hohendanner F: "Isolation of Atrial Cardiomyocytes from a Rat Model of Metabolic Syndrome-related Heart Failure with Preserved Ejection Fraction," *J Vis Exp* 2018(137).

Solutions and chemicals. Chemicals were obtained from Sigma-Aldrich (St. Louis, MO, USA) unless noted otherwise. The dual SGLT1/2 inhibitor sotagliflozin was provided by Lexicon Pharmaceuticals (The Woodlands, TX, USA). Fluorescent dyes Fura-2 AM, Rhod-2 AM, MitoTracker red, MitoTracker green, TMRE and H2-DCF were obtained from Thermo Fisher Scientific (Waltham, MA, USA). Tyrode solution contained (in mM): 130 NaCL, 4 KCl, 2 CaCl, 1 MgCl2, 10 Glucose, 10 HEPES; pH adjusted to 7.4 with NaOH. LA cardiomyocytes were plated on laminin-coated glass coverslips. 20 mM caffeine was added to Tyrode solution to induce sarcoplasmic reticulum (SR) $Ca^{2+}$ release and obtain a measure of SR $Ca^{2+}$ content. See FIGS. 2F, 2G. For baseline recordings of $Ca^{2+}$ transient (CaT), sarcomere shortening and arrhythmic events (FIGS. 1C-F, 2A-E, 3A-F), Tyrode solution containing 3 mM $Ca^{2+}$ was used. For glucose starvation (FIGS. 2H-J, 5A-D), glucose of Tyrode solution was replaced with 30 mM mannitol. For subsequent glucose reintroduction, mannitol was replaced with 30 mM glucose ("high glucose condition").

For cell membrane permeabilization and subsequent measurements of mitochondrial $Ca^{2+}$ uptake (See 'Mitochondrial structure and $Ca^{2+}$ uptake') wash and internal solutions were used. Wash solution contained (in mM): 100 potassium acetate, 15 KCl, 0.35 EGTA, 0.75 $MgCl_2$, 10 HEPES; pH adjusted to 7.2 with KOH. Internal solution contained (in mM): 125 KCl, 10 NaCl, 20 HEPES, 5 pyruvate, 2 maleic acid, 2 glutamic acid, 0.5 KH2PO4, 0.5 $MgCl_2$, 5 EGTA, 0.002 free $Ca^{2+}$ (MaxChelator), 15 BDM, pH adjusted to 7.2 with KOH. For permeabilization, 0.005% saponin was added to the internal solution.

Fluorescent dyes were used at the following concentration (in mM): 0.002 Fura, 1 Rhod-2, 1 Mitotracker, 0.01 H2-DCF, 50-6 TMRE.

For Western blot analysis, LA tissue was homogenized in lysis buffer. Lysis buffer contained (in mM): 137 NaCl, 20 NaF, 1 sodium pyrophosphate, 50 β-glycerophosphate, 10 EDTA, 1 EGTA, 1 PMSF, 10% glycerol, 1% NP 40, 4 μg/ml aprotinin 4 μg/ml pepstatin A, 4 μg/ml leupeptin.

$Ca^{2+}$ measurements and sarcomere shortening. Radiometric $Ca^{2+}$ measurements (excitation: 340 nm and 385 nm, emission: 510±10 nm; $[Ca^{2+}]$ expressed as the ratio R=F340/F380) were performed either with a CytoCypher MultiCell System (CytoCypher BV, Netherlands; FIGS. 1C-F, 2D-G, 4A-F) or an Axiovert 200 microscope (Zeiss, Oberkochen, Germany) fluorescence imaging assembly (FIGS. 2A-C, 2H-J, 3A-E, 6E-I). LA cardiomyocytes were loaded with Fura-2 for 30 min at room temperature, washed twice with Tyrode solution and transferred to the microscope. Experiments were conducted at 37° C. and CaT were recorded at steady state (following electric stimulation).

CaT and sarcomere shortening of LA and LV cardiomyocytes were recorded for 10 s at 3 Hz stimulation. See FIGS. 2D-G, 4A-F. Electric stimulation was turned off and spontaneous SR $Ca^{2+}$ release events (See Voigt N, Heijman J, Wang Q, Chiang D Y, Li N, Karck M, Wehrens X H T, Nattel S, Dobrev D: "Cellular and molecular mechanisms of atrial arrhythmogenesis in patients with paroxysmal atrial fibrillation," *Circulation* 2014, 129(2):145-156) (SCaEs) immediately recorded for a duration of 10 s (FIG. 1C-F). In a sub-set of LA cells, CaT were recorded for 10 s at 1 Hz stimulation. Electric stimulation was turned off, the cells immediately exposed to 20 mM caffeine and the sub-sequent caffeine-induced CaT recorded for 10 s (FIG. 2A-C, 3A-E). Sodium-calcium exchanger (NCX) activity was calculated as previously described. See Hohendanner F, Walther S, Maxwell J T, Kettlewell S, Awad S, Smith G L, Lonchyna V A, Blatter L A: "Inositol-1,4,5-trisphosphate induced $Ca^{2+}$ release and excitation-contraction coupling in atrial myocytes from normal and failing hearts," J Physiol 2015, 593(6):1459-1477.

For measurement under different metabolic conditions, LA cardiomyocyte CaT were recorded for 10 s at 1 Hz. See FIGS. 5E-1. Cells were treated with 2-deoxyglucose to inhibit glycolysis for a duration of 3 min, while maintaining steady stimulation at 1 Hz and CaT were recorded for another 10 s. A sub-set of cells was starved of glucose for 1 h at 37° C. CaT were recorded for 10 s at 1 Hz stimulation. See FIGS. 2H-J. Cells were exposed to glucose and constant electric pacing at 1 Hz was maintained. After 1 min, CaT transients were recorded for 10 s at 1 Hz stimulation.

Mitochondrial structure and $Ca^{2+}$ uptake. Mitochondrial structure was visualized by local thresholding of two-dimensional images acquired with MitoTracker Red (FIGS. 5A-B, 6D) and MitoTracker Green (FIGS. 4C-F) at an LSM 800 laser scanning microscope (Zeiss, Oberkochen, Germany). The fraction of mitochondria in relation to cell surface was taken as a measure of mitochondrial density. The averaged perimeter to area ratio of mitochondrial structures per cell was calculated as an indicator of mitochondrial fission using a 2-step Otsu thresholding algorithm. See Hohendanner F, Ljubojevic S, MacQuaide N, Sacherer M, Sedej S, Biesmans L, Wakula P, Platzer D, Sokolow S, Herchuelz A et al: "Intracellular dyssynchrony of diastolic cytosolic [Ca(2)(+)] decay in ventricular cardiomyocytes in cardiac remodeling and human heart failure," *Circ Res* 2013, 113(5):527-538.

Mitochondrial $Ca^{2+}$ uptake was determined as previously described in detail. See Maxwell J T, Tsai C H, Mohiuddin T A, Kwong J Q: "Analyses of Mitochondrial Calcium Influx in Isolated Mitochondria and Cultured Cells," *Journal of visualized experiments: JoVE* 2018(134). LA cardiomyocytes were loaded with Rhod-2 AM and MitoTracker green, transferred to an LSM 800 laser scanning microscope and washed twice with sodium and calcium-free wash solution. The cells were then permeabilized with internal solution containing 0.005% saponin for a duration of 30-60 s and consecutively washed twice with nominal $Ca^{2+}$ free internal solution containing 5 mM EGTA. Two-dimensional images of Rhod-2 (excitation: 559 nm, emission: 575-675 nm) and MitoTracker green fluorescence (excitation: 488 nm, emission: 505-525 nm) were obtained. The perfusion was switched to internal solution containing 2 μM $Ca^{2+}$. After 1 min, a second set of Rhod-2/MitoTracker images was obtained. Following another 1-min interval, a third set of images was obtained to confirm that mitochondrial $Ca^{2+}$ uptake had indeed been completed in the second set. A binary mask of mitochondrial structures was derived from MitoTracker green images and positive pixels defined as the region-of-interest for sub-sequent determination of Rhod-2 signal intensity (F). Signal intensity during perfusion with 0 μM $Ca^{2+}$ was defined as F0 and changes of $[Ca^{2+}]$ after exposure to 2 μM $Ca^{2+}$ expressed as ΔF=F−F0. The change of mitochondrial density (Δ%) was quantified as a measure of mitochondrial swelling.

Mitochondrial depolarization. LA cardiomyocytes were loaded with TMRE and MitoTracker green, transferred to an LSM 800 laser scanning microscope and kept in Tyrode's solution containing 2 mM $Ca^{2+}$ and 10 nM TMRE. Two-dimensional images of TMRE (excitation: 561 nm, emission: 565-585 nm) and MitoTracker green fluorescence (excitation: 488 nm, emission: 505-525 nm) were acquired for a duration of 6 min (interval: 2 s, resolution: 512×512 px, pixel size: 1.25 μm, pixel time: 1.03 μs, laser intensity: 4%). A binary mask of both channels was derived using a Bernsen thresholding algorithm (ImageJ). Positive pixels of the MitoTracker green image were defined as mitochondria and a positive overlay of the TMRE image assumed to indicate a polarized state. The standard deviation of polarized mitochondria over time was taken as a measure of spatiotemporal oscillation.

ROS production. LA cardiomyocytes were starved of glucose for 1 h at 37° C., loaded with H2-DCF and transferred to an LSM 800 laser scanning microscope. Two-dimensional images (excitation: 488 nm, emission: 505-252 nm) were acquired for a duration of 30 s (interval: 2 s, resolution: 256×256 px, pixel size: 0.624 μm, pixel time: 8.24 μs, laser intensity: 0.6%). Cells were exposed to 30 mM glucose and another set of images acquired for a duration of 90 s. Image sequences acquired between 0-30 s (glucose starved) and 90-120 s (glucose saturated) were individually assessed. H2-DCF signal intensity (F) of the initial image was defined as F0, reactive oxygen species (ROS) accumulation calculated as $\Delta F=F-F0$ per image, averaged per image sequence and reported as the respective rate $\Delta F/(F0*t)$.

Western Blots. LA tissue homogenate was run on a 4-12% Bis-Tris gel and transferred to a 0.45 μm nitrocellulose membrane for 120 min. The total protein on the membrane was stained with Ponceau S. Non-specific binding was blocked with 5% dried milk in Tris-buffered saline (pH 7.4) containing 0.1% Tween-20. Membranes were probed with anti-SGLT-1 (biomol, Germany), anti-SGLT-2 (abcam, UK & Santa Cruz, CA, US). Anti-mouse IgG linked with IRDye 680RD or anti-rabbit IgG linked with 800CW (LI-COR) were used as a secondary antibody. The signal was recorded with an Odyssey CLx System. Band intensities and total protein were determined by Image Studio software (LI-COR).

Data analysis and statistics. Results are shown as mean±standard error. A p-value of <0.05 was considered to be of statistical significance.

Experimental Results

LA/LV interaction and sotagliflozin mitigating left atrial enlargement and arrhythmic $Ca^{2+}$ release in HFpEF were studied. In vivo LA volume obtained via echocardiography showed severely enlarged atria in the HFpEF group. LA enlargement correlated with LV function. In-vitro, LV and LA cardiomyocytes correlated regarding diastolic $[Ca^{2+}]$ ($R^2$=0.98) and regarding (the closely related) diastolic sarcomere length ($R^2$=0.63), indicative of LV/LA interaction in this HFpEF atrial cardiomyopathy model. Spontaneous $Ca^{2+}$ release events (SCaEs) of LA cardiomyocytes were more frequent and their $Ca^{2+}$ release amplitude increased in HFpEF.

It was found that sotagliflozin mitigates LA enlargement in HFpEF. Even though the event frequency remained unaltered, the amplitude of SCaEs in HFpEF was significantly reduced following sotagliflozin treatment. Overall, LA volume in vivo correlated with the occurrence of SCaEs in-vitro, indicating mechanical stretch of cardiomyocytes (as determined by volumetric load in vivo) to be a potential modulator of arrhythmic SR $Ca^{2+}$ release in this model. See FIG. 1F.

Figure 2:
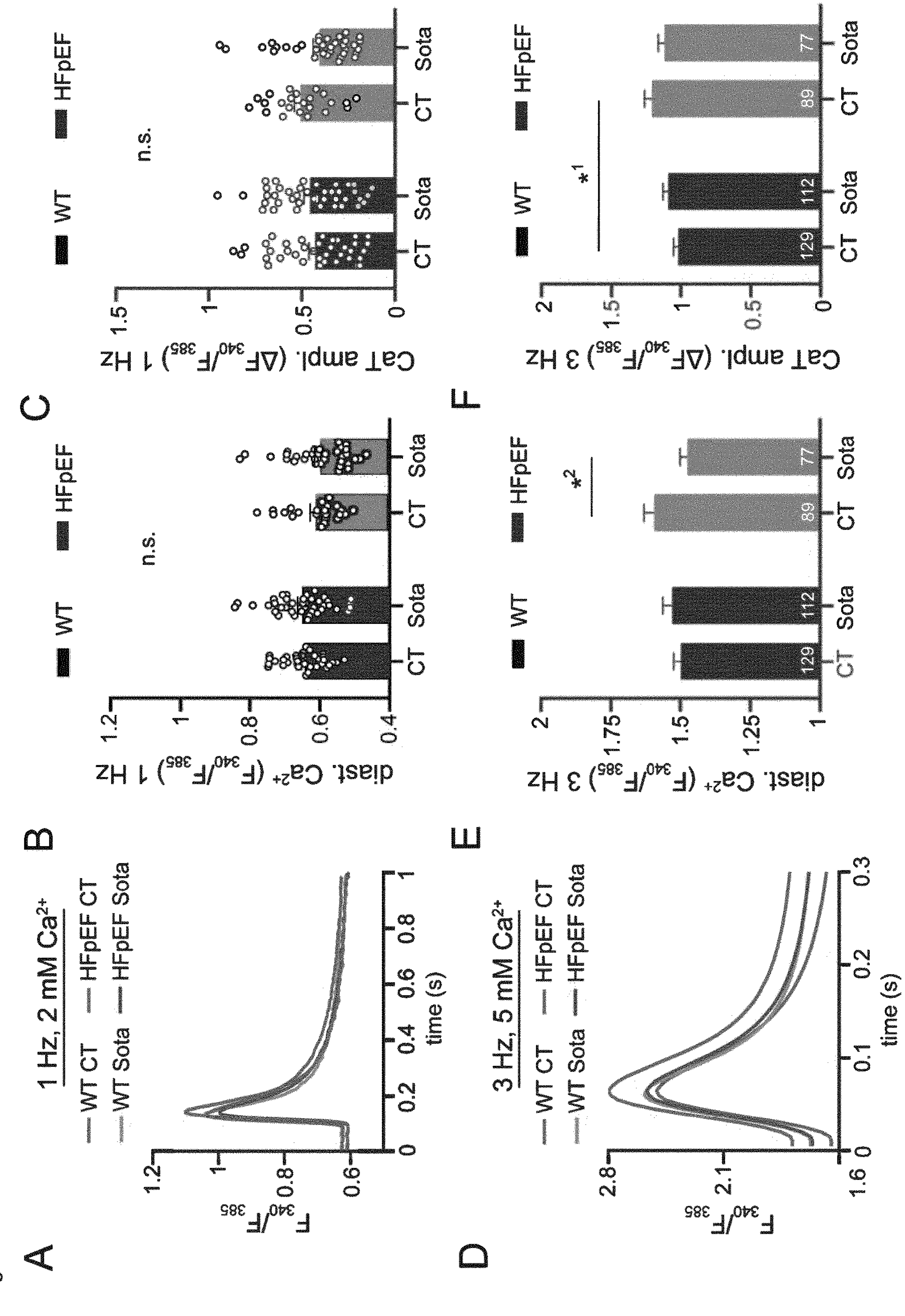
FIG. 2. (A) Representative examples of CaT during 1 Hz electric stimulation and 2 mM extracellular $[Ca^{2+}]$. Related data of (B) diastolic $Ca^{2+}$ and (C) CaT amplitude. (D) Averaged CaT (all cells per group) during 3 Hz electric stimulation and 5 mM extracellular [$Ca^{2+}$]. Related data of (E) diastolic $Ca^{2+}$, (F) CaT amplitude and (G) time-to-peak. (H) Representative examples of CaT at 1 Hz electric stimulation after 1 h incubation in glucose-deprived buffer (left) and after reintroduction of 30 mM glucose for 1 min (right). Dashed lines indicate diastolic $Ca^{2+}$ at baseline, arrows indicate stimulation triggers. (I) Related data of diastolic $Ca^{2+}$ before (man) and after treatment with glucose (glc); (J) change of diastolic $Ca^{2+}$. Statistical analysis: Two-way ANOVA followed by post-hoc Bonferroni. p-values: [1]0.03, [2]0.02, [3]0.01, [4]<0.001, [5]0.001, [6]0.046. n=cells derived from 6 animals per group.
Figure 2:
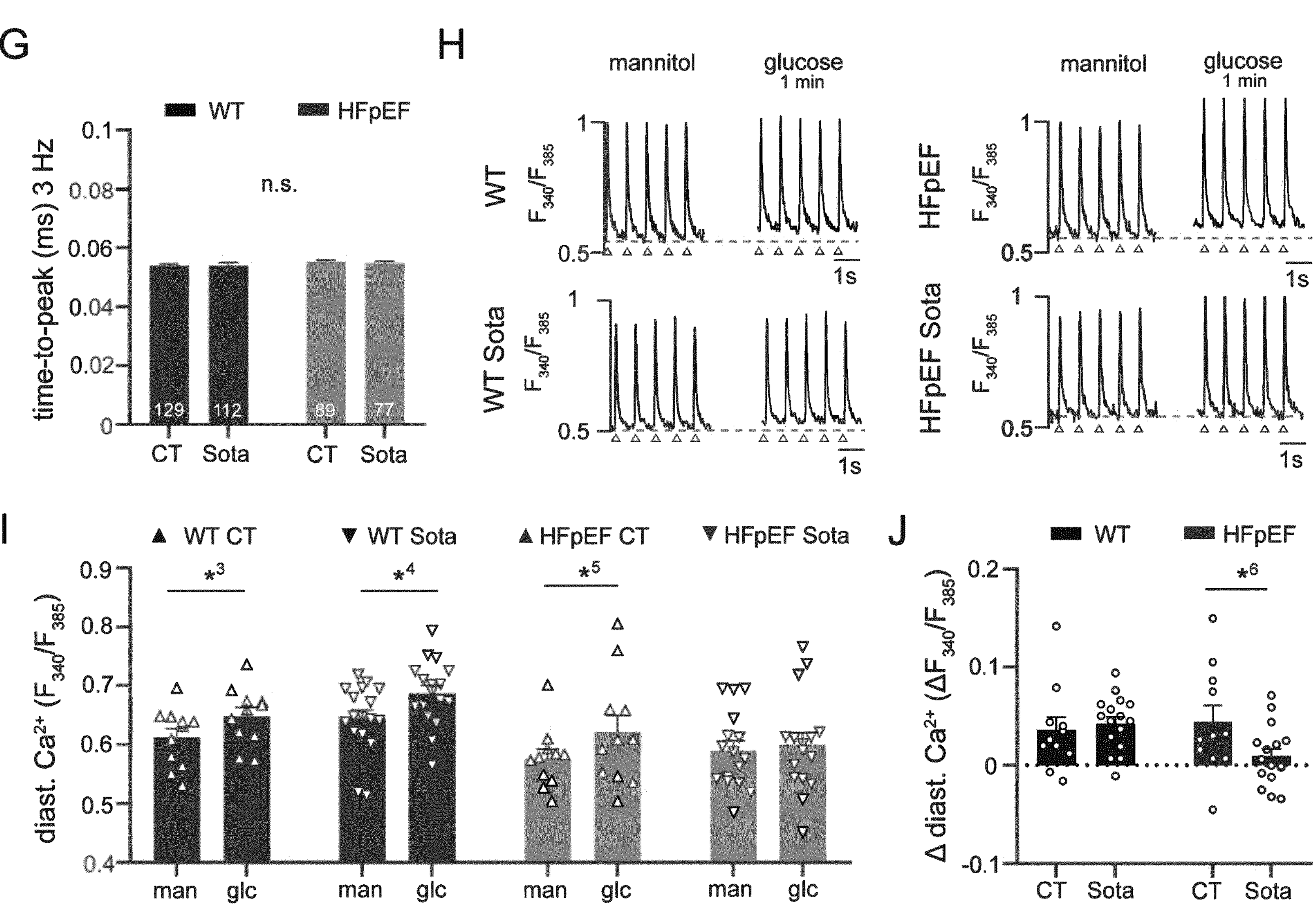
Figure 3:
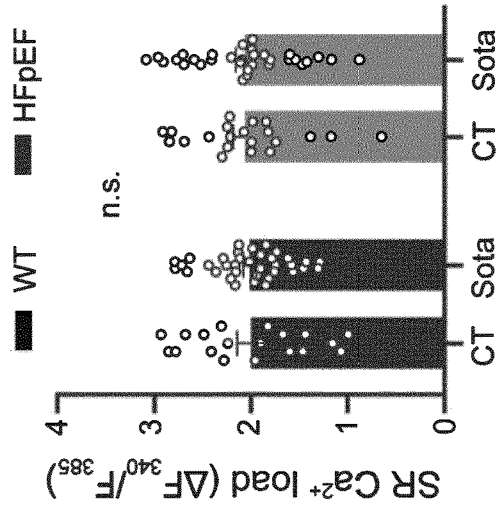
FIG. 3. (A) Representative examples of electrically (1 Hz; left) and caffeine-induced (20 mM; right) CaT. Tau of decay was determined during electric stimulation (left; blue curvature) and after caffeine (right; orange curvature). Blue arrows indicate electric stimulation triggers, orange arrows indicate caffeine application. Related data of (B) SR $Ca^{2+}$ load, (C) tau of electrically stimulated CaT (D), tau of caffeine-induced CaT and (E) NCX forward-mode activity (calculated from C and D). Statistical analysis: Two-way ANOVA followed by post-hoc Bonferroni. p-values: [1]0.008, [2]0.01, [3]0.01. n=cells derived from 6 animals per group.
Figure 3:
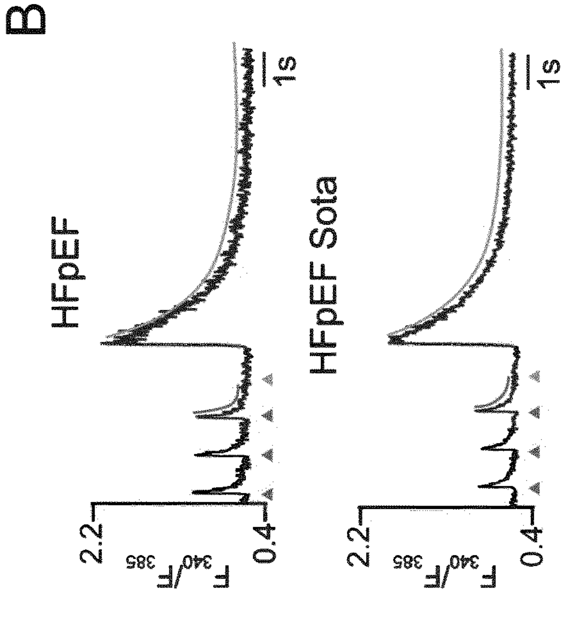
Figure 3:
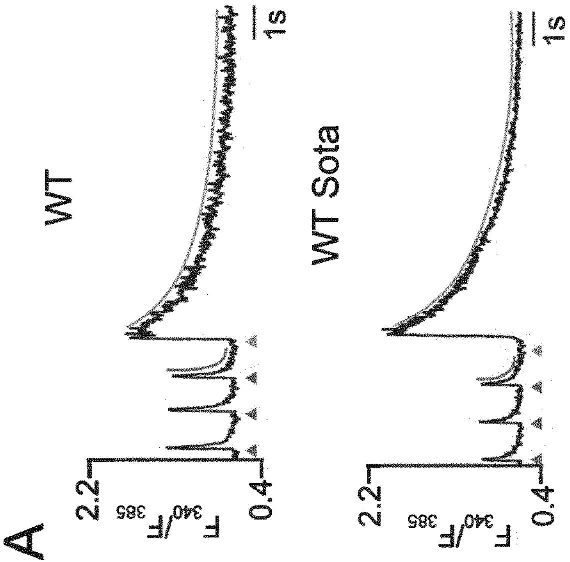
Figure 3:
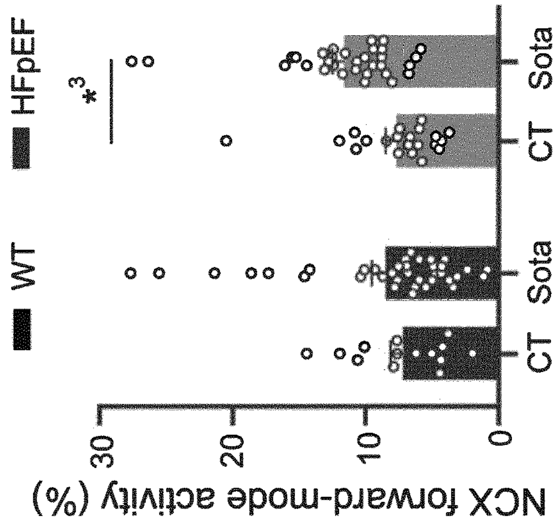
Figure 3:
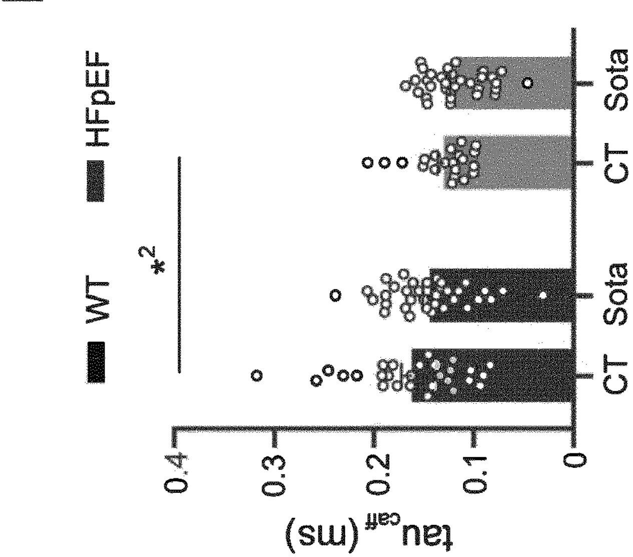
Figure 3:
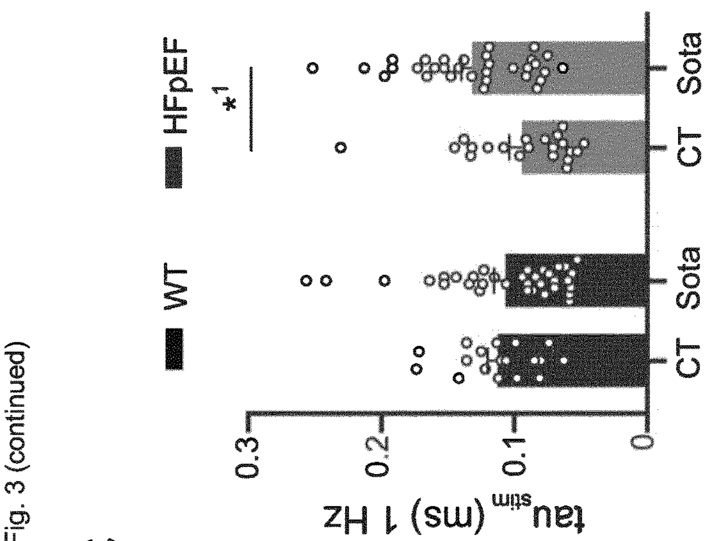
Figure 4:
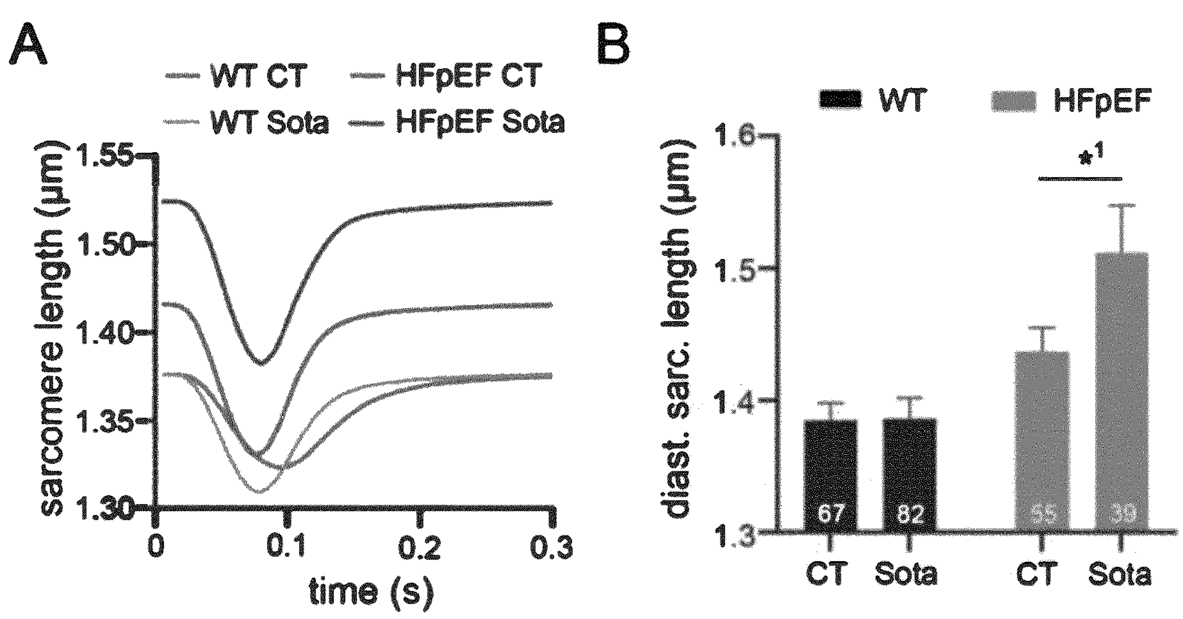
FIG. 4. (A) Representative examples of sarcomere shortening during 3 Hz electric stimulation and 5 mM extracellular [$Ca^{2+}$]. Related data of (B) diastolic sarcomere length, (C) sarcomere shortening, (D) time-to-peak and (E) RT50 of decay. (F) Relationship of averaged CaT (FIG. 2A) and averaged sarcomere shortening (FIG. 3A). Statistical analysis: Two-way ANOVA followed by post-hoc Bonferroni. p-values: [1]0.03, [2]<0.001, [3]<0.001, [4]<0.001, [5]<0.001, [6]<0.001. n=cells derived from 6 animals per group.
Figure 4:
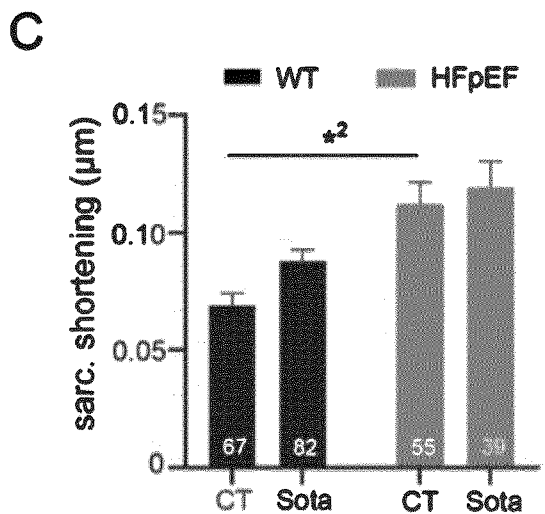
Figure 4:
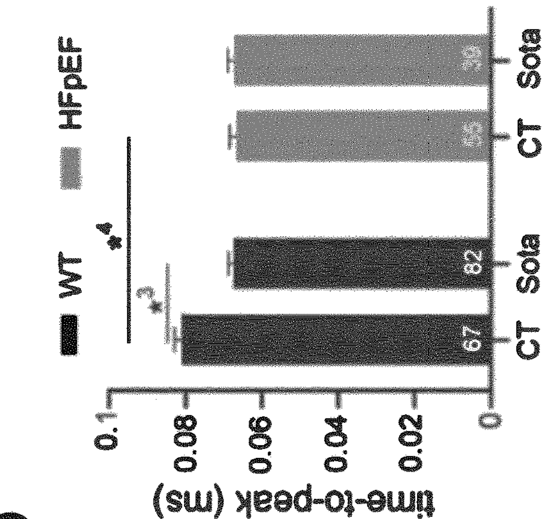
Figure 4:
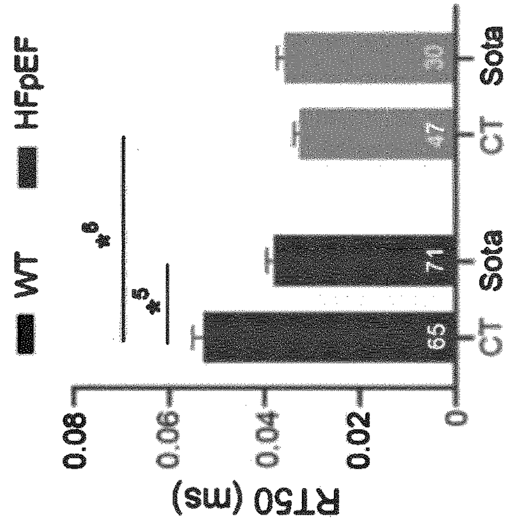
Figure 4:
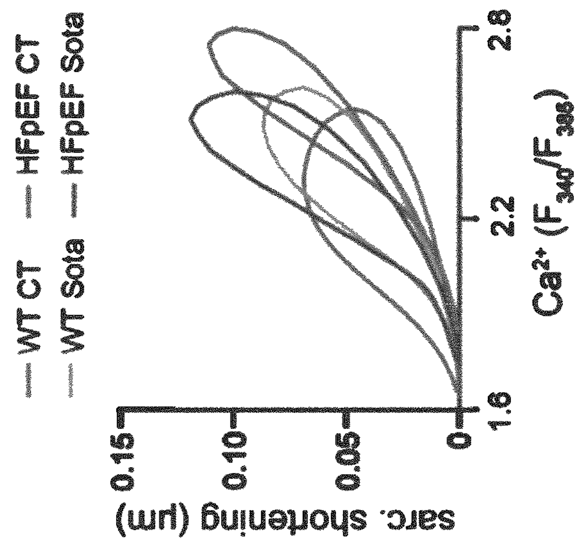
Figure 5:
FIG. 5. (A) Representative examples of mitochondrial structure in LA cardiomyocytes (dye: MitoTracker after thresholding) and (B) related data of mitochondrial density. (C) Representative example of mitochondrial structure of LA cardiomyocytes after permeabilization of the sarcolemma (above), mitochondrial $Ca^{2+}$ during perfusion with internal solution containing either 0 μM (center) or 2 μM $Ca^{2+}$ (below). (D) Related data of mitochondrial $Ca^{2+}$ uptake, (E) mitochondrial density and (F) correlation of mitochondrial $Ca^{2+}$ uptake and mitochondrial swelling. (G) Serum concentration of 8-hydroxybutyrate (BHB). Statistical analysis: Two-way ANOVA followed by post-hoc Bonferroni (B, E, G) or unpaired, two-tailed Student's t-test (D). p-values: [1]0.004, [2]<0.001, [3]<0.001, [4]<0.001, [5]0.026, [6]0.049. (A-F) n=cells derived from 6 animals per group. (G) n=animals.
Figure 5:
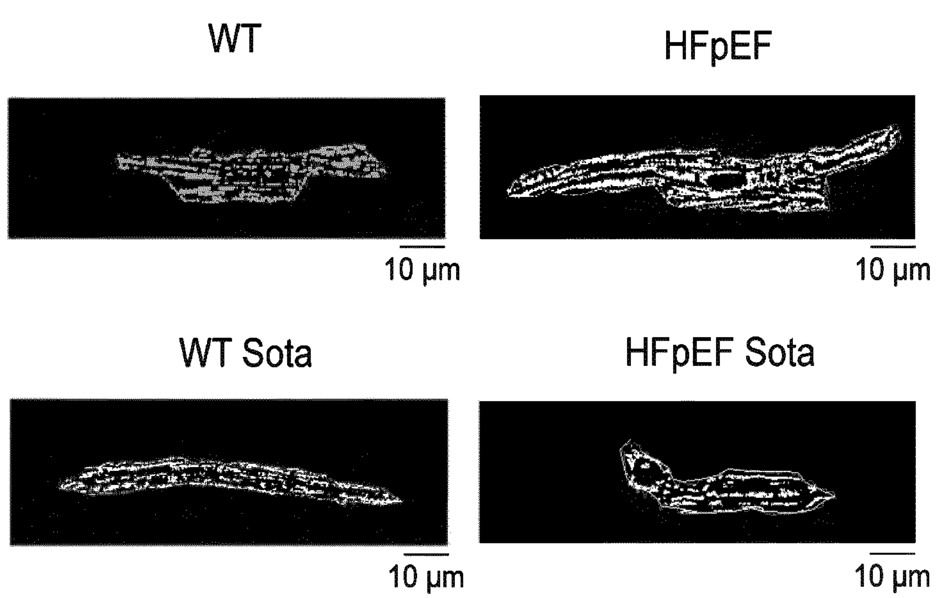
Figure 5:
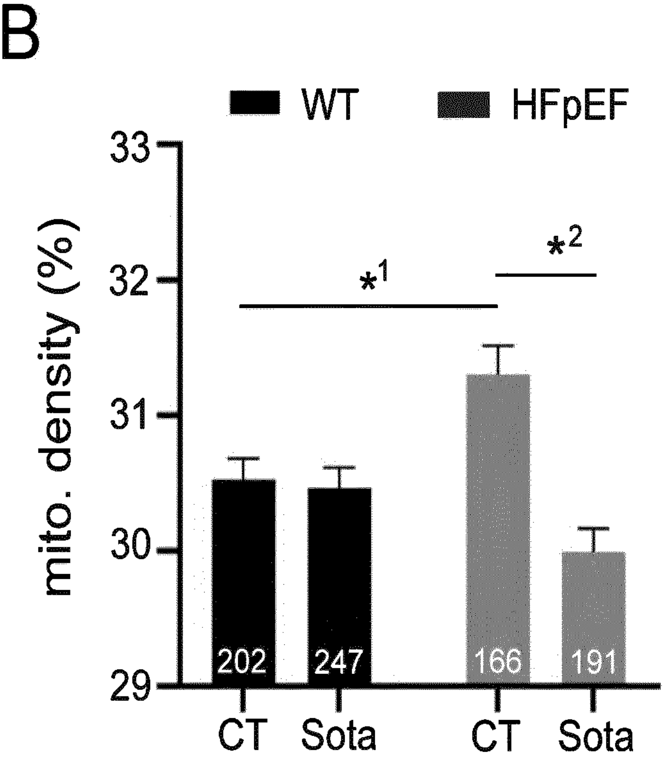
Figure 5:
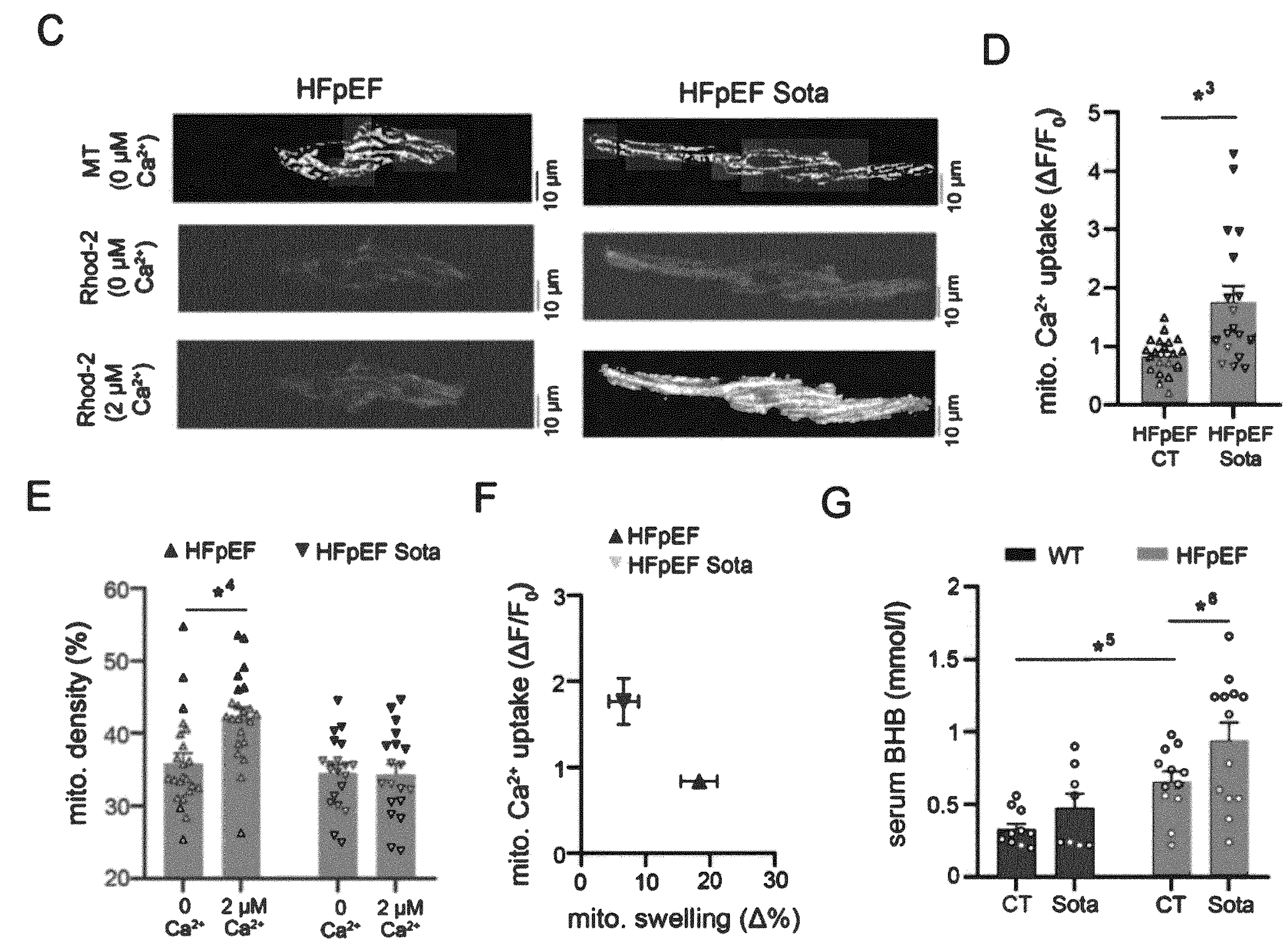
Figure 6:
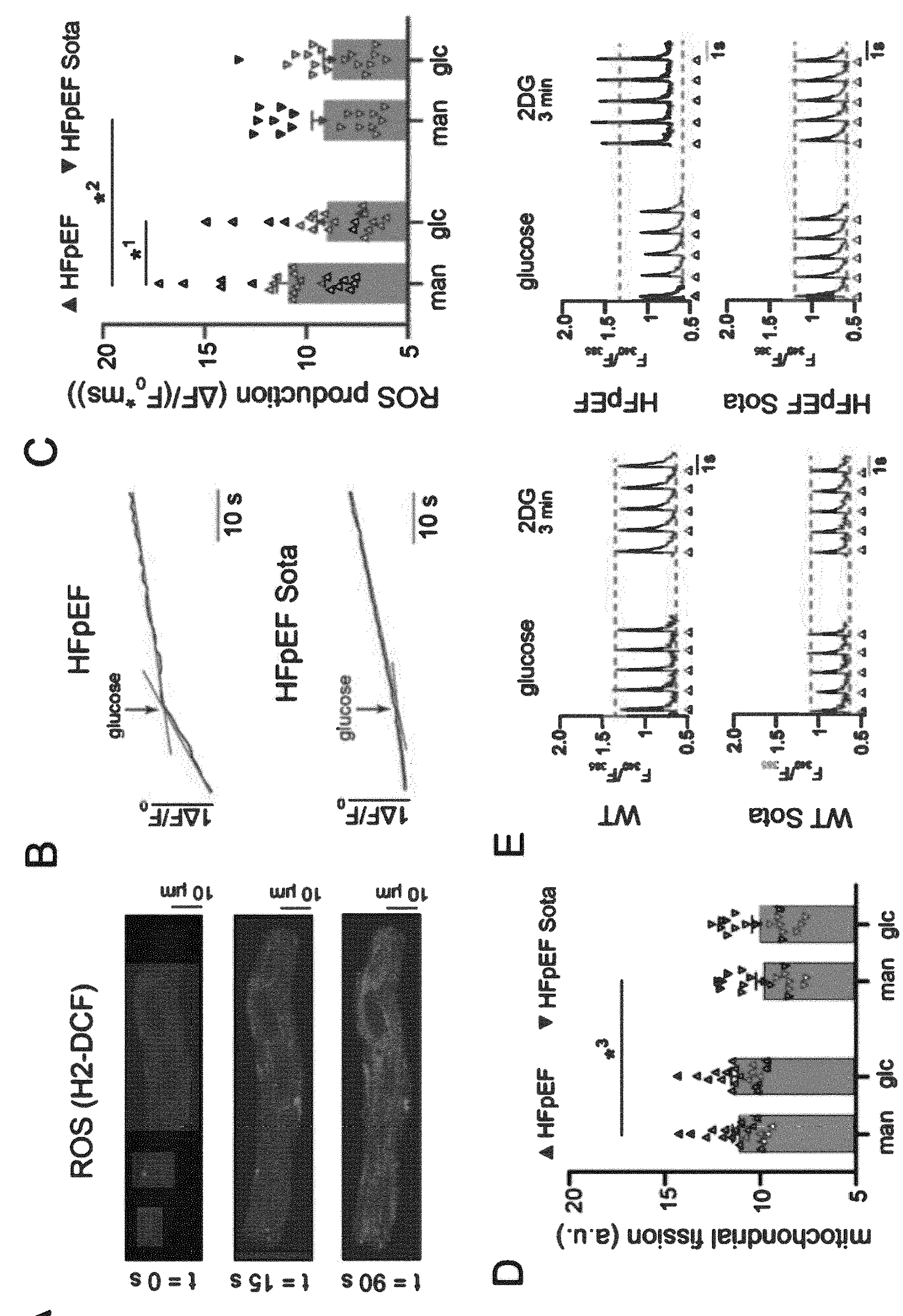
FIG. 6. (A) Example image sequence of ROS measurements in LA cardiomyocytes (shown: HFpEF). (B) Representative example and (C) related data of ROS production after 1 h incubation in glucose-deprived buffer (man) and after 30 s of glucose reintroduction (glc). (D) Mitochondrial fission of LA cardiomyocytes after 1 h incubation in glucose-deprived buffer (man) and after 60 s of glucose reintroduction (glc). (E) Representative examples of CaT at 1 Hz electric stimulation before (left) and 3 min after glycolytic inhibition with 2-deoxyglucose (2DG; right). Red, dashed lines indicate CaT peak (upper) and diastolic $Ca^{2+}$ (lower) at baseline, arrows indicate stimulation triggers. Related data of (F) Diastolic $Ca^{2+}$ and (H) CaT amplitude before (glc) and after glycolytic inhibition (2DG); (G) corresponding change of diastolic $Ca^{2+}$ and (I) CaT amplitude. Statistical analysis: Two-way ANOVA followed by post-hoc Bonferroni. p-values: [1]<0.001, [2]0.046, [3]0.015, [4]0.005, [5]0.007, [6]0.01, [7]0.04, [8]0.02, [9]0.016. n=cells derived from 6 animals per group.
Figure 6:
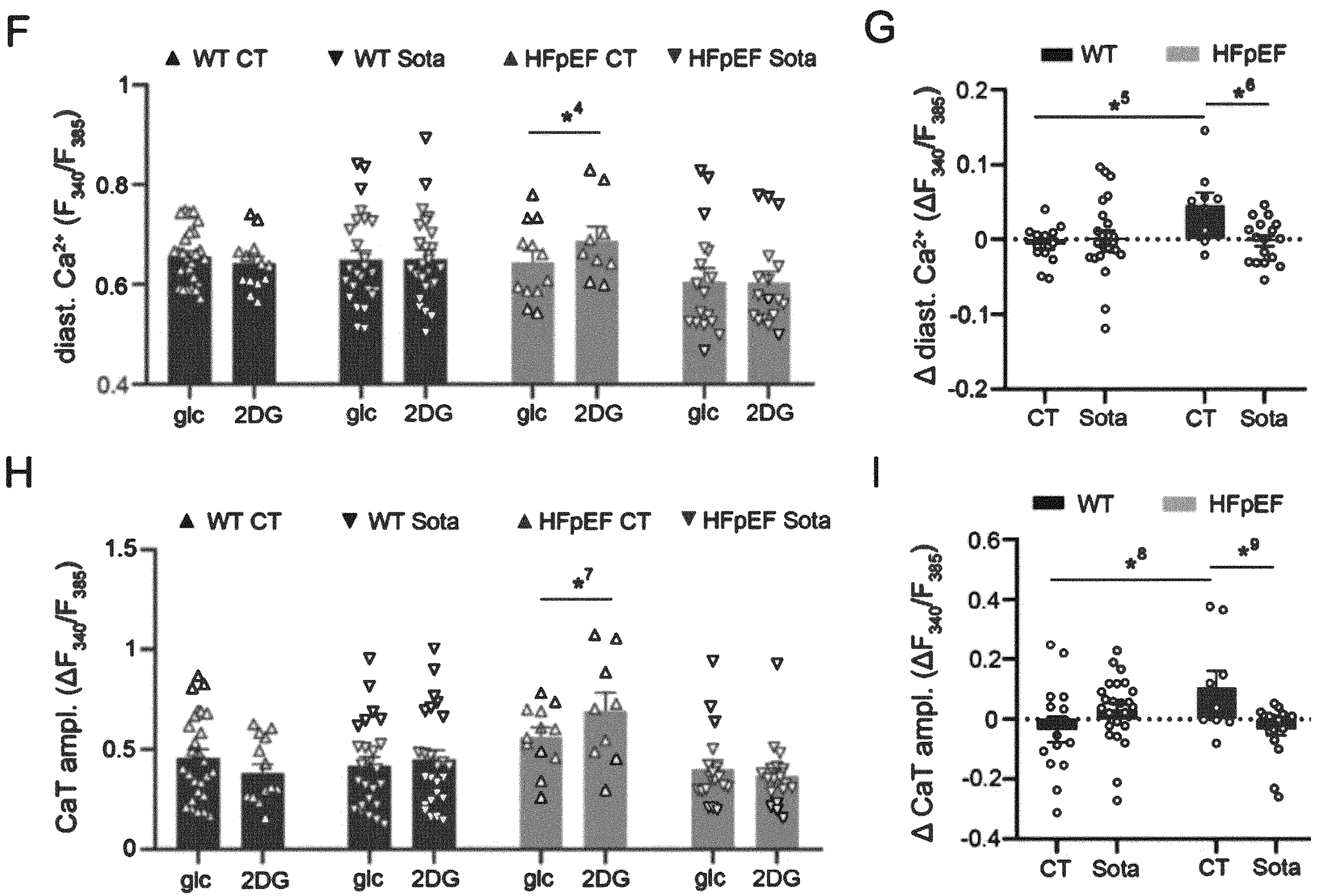

It was found that sotagliflozin lowers diastolic $Ca^{2+}$ in LA cardiomyocytes in HFpEF. First, the CaT of LA cardiomyocytes was examined at 1 Hz stimulation and 2 mM extracellular $[Ca^{2+}]$. See FIG. 2A. No differences could be observed in diastolic $Ca^{2+}$ and CaT amplitude in HFpEF vs. WT. See FIGS. 2B-C. The cells were then challenged with increased stimulation frequencies (3 Hz) and extracellular $[Ca^{2+}]$ (5 mM; FIG. 2D). Again, no difference was observed diastolic $Ca^{2+}$, although CaT amplitudes in HFpEF were increased. See FIGS. 2E-F. Time-to-peak remained unchanged. In order to assess the effect of glucose influx on cytosolic $[Ca^{2+}]$, LA cardiomyocytes were starved of glucose for 1 h in Tyrode's solution containing 30 mM mannitol and consecutively challenged with 30 mM glucose. Both HFpEF and WT showed an increase in diastolic $[Ca^{2+}]$ at a similar extent. See FIGS. 2I-J. Chronic treatment with sotagliflozin did not alter diastolic $[Ca^{2+}]$ and CaT amplitude at baseline (1 Hz, 2 mM $Ca^{2+}$). When challenged with 3 Hz and 5 mM extracellular $[Ca^{2+}]$ however, sotagliflozin lead to a significant reduction of diastolic $[Ca^{2+}]$ in HFpEF, while leaving CaT amplitudes unchanged. Interestingly, sotagliflozin also prevented glucose-mediated influx of diastolic $Ca^{2+}$ in HFpEF.

It was found that sotagliflozin increases NCX forward-mode activity in HFpEF. CaT of LA cardiomyocytes were recorded during electric stimulation and after the application of caffeine in order to assess SR $Ca^{2+}$ load, as well as the relative contribution of NCX activity towards cytosolic $Ca^{2+}$ removal. See FIG. 3A. In HFpEF, SR $Ca^{2+}$ load and tau of decay during paced CaT remained unchanged. See FIGS. 3B-C. Tau of decay of caffeine-induced CaT however was significantly shorter in HFpEF. See FIG. 3D. The contribution of NCX forward-mode activity to cytosolic $[Ca^{2+}]$ removal in paced CaT was unaltered in HFpEF. See FIG. 3E. Treatment with sotagliflozin had no effect on SR $Ca^{2+}$ load in HFpEF. In HFpEF, tau of decay was significantly prolonged in with Sota, yet tau of caffeine-induced CaT was unchanged. Interestingly, this resulted in a ~50% increased contribution of NCX forward-mode activity on cytosolic $Ca^{2+}$ removal (7.6±0.7 vs. 11.6±0.7%, n=14 and 21 cells).

It was found that sotagliflozin lengthens sarcomeres during diastole in HFpEF. The effect of sotagliflozin on cardiomyocyte mechanics was also investigated. See FIG. 4A. Diastolic sarcomere length remained unaltered in HFpEF vs. WT. In support of the notion of a rather compensatory atrial phenotype (See Hohendanner F, Bode D, Primessnig U, Guthof T, Doerr R, Jeuthe S, Reimers S, Zhang K, Bach D, Wakula P et al: "Cellular mechanisms of metabolic syndrome-related atrial decompensation in a rat model of HFpEF," *J Mol Cell Cardiol* 2018, 115:10-19), HFpEF cardiomyocytes showed an increased sarcomere shortening, shorter time-to-peak and relaxation time vs. WT. See FIGS. 4C-E. Sotagliflozin led to a significant increase of diastolic sarcomere length in HFpEF. In WT, sotagliflozin shortened time-to-peak and relaxation time, while this effect could not be observed in HFpEF. Overall, sotagliflozin reduced $Ca^{2+}$ sensitivity in HFpEF. See FIG. 4F.

It was found that sotagliflozin prevents mitochondrial swelling and increases mitochondrial $Ca^{2+}$ uptake in HFpEF. To further elucidate how sotagliflozin mitigated atrial in vivo remodeling and decreased the propensity for pro-arrhythmic $Ca^{2+}$ release, mitochondrial structure (FIGS. 5A-B) and $Ca^{2+}$ uptake were measured. See FIGS. 5C-D. An increased density of mitochondria in LA cardiomyocytes could be observed in HFpEF, which was prevented by sotagliflozin. Treatment with sotagliflozin led to a two-fold increase of mitochondrial $Ca^{2+}$ uptake in HFpEF (0.84±0.07 vs. 1.76±0.27 AF/F0, n=21 and 18 cells from 6 animals/group) in permeabilized cells after exposure from 0 μM to 2 μM $Ca^{2+}$. Additionally, a notable swelling of mitochondria was visible in HFpEF cells (35.9±1.8 to 42.4±1.6%, n=21 cells and 18 cells from 6 animals), while this effect did not occur with sotagliflozin. See FIGS. 5E-F. Analysis of circulating ketone bodies revealed a shift in the availability of mitochondrial fuel: HFpEF showed an increased concentration of β-hydroxybutyrate compared to the control group, which was even further enhanced by sotagliflozin treatment. See FIG. 5G. Differences in the incidence and spatial distribution of mitochondrial depolarizations could not be detected.

It was found that sotagliflozin improves metabolic dysfunction during glucose depletion in HFpEF. As impaired myocardial glucose metabolism and increased oxidative stress are hallmark features of heart failure and acute decompensation (See Kolijn D, Pabel S, Tian Y, Lodi M, Herwig M, Carrizzo A, Zhazykbayeva S, Kovacs A, Fulop G A, Falcao-Pires I et al: "Empagliflozin improves endothelial and cardiomyocyte function in human heart failure with preserved ejection fraction via reduced pro-inflammatory-oxidative pathways and protein kinase Galpha oxidation," *Cardiovasc Res* 2020), glucose depletion was used to further challenge HFpEF cardiomyocytes. Sotagliflozin significantly reduced ROS production (FIGS. 6A-C) and mitochondrial fission of LA cardiomyocytes after 1 h glucose starvation in HFpEF. See FIG. 6D. ROS production in HFpEF decreased after reintroduction of glucose, while this effect could not be observed with sotagliflozin. In line with this, sotagliflozin also prevented an increased influx of diastolic $Ca^{2+}$ and an increased CaT amplitude gain upon glycolytic inhibition with 2-deoxyglucose in HFpEF. See FIGS. 6E-I. Under baseline conditions, antioxidative treatment with acetylcysteine decreased the occurrence of SCaEs in LA cardiomyocytes in both HFpEF groups.

It was found that chronic treatment with the dual SGLT1/2 inhibitor sotagliflozin was effective in mitigating LA cardiomyopathy in a rat model of metabolic syndrome related HFpEF. In HFpEF, sotagliflozin decreased the magnitude of arrhythmic $Ca^{2+}$ release events of LA cardiomyocytes in-vitro. Sotagliflozin reduced cytosolic $[Ca^{2+}]$ at baseline, as well as in response to glucose influx and depletion. Lower cytosolic $[Ca^{2+}]$ was accompanied by an increased $Ca^{2+}$ buffer capacity of the mitochondrial compartment, decreased mitochondrial swelling at baseline and lower ROS production during glucose depletion.

In human right atria, previous work by Voigt et al. has highlighted the role of pro-arrhythmic SCaEs of cardiomyocytes in persistent AF. See Voigt N, Heijman J, Wang Q, Chiang D Y, Li N, Karck M, Wehrens X H T, Nattel S, Dobrev D: "Cellular and molecular mechanisms of atrial arrhythmogenesis in patients with paroxysmal atrial fibrillation," *Circulation* 2014, 129(2):145-156. The authors describe an increased SCaE incidence and $Ca^{2+}$ release amplitude, accompanied by alterations of intrinsic $Ca^{2+}$ cycling, i.e., enhanced SERCA function, increased CaT amplitude, larger RyR-mediated $Ca^{2+}$ leak and unaltered NCX activity. The present model is not known to be a dedicated AF model and overt AF was not found in the present studies. However, atrial remodeling and atrial cardiomyopathy are entities preceding the presence of AF. Goette A, Kalman J M, Aguinaga L, Akar J, Cabrera J A, Chen S A, Chugh S S, Corradi D, D'Avila A, Dobrev D et al: "EHRA/HRS/APHRS/SOLAECE expert consensus on Atrial cardiomyopathies: Definition, characterisation, and clinical implication," *J Arrhythm* 2016, 32(4):247-278. In support of this notion, this study and previous work show an overall similar cellular phenotype regarding $Ca^{2+}$ handling in HFpEF-related LA remodeling. See, e.g., Hohendanner F, Bode D, Primessnig U, Guthof T, Doerr R, Jeuthe S, Reimers S, Zhang K, Bach D, Wakula P et al: "Cellular mechanisms of metabolic syndrome-related atrial decompensation in a rat model of HFpEF," *J Mol Cell Cardiol* 2018, 115:10-19. This indicates a common denominator of pro-arrhythmogenic atrial remodeling, potentially associated with a progression towards AF. Chronic dual SGLT1/2 inhibition led to a reduction of SCaE amplitudes in HFpEF, yet the incidence of events remained unaffected. See FIGS. 1E-F. This observation can be explained by an increased NCX forward-mode activity: Enhanced $Ca^{2+}$ extrusion mitigates cytosolic $Ca^{2+}$ overload (i.e., ryanodine receptor-mediated leak) and unburdens intrinsic $Ca^{2+}$ buffer systems (i.e., mitochondria). This potentially alleviates pro-arrhythmic organ-wide events as it also impacts $Ca^{2+}$ wave propagation and limits spontaneous cytosolic $Ca^{2+}$ induced $Ca^{2+}$ release. Hohendanner F, Maxwell J T, Blatter L A: "Cytosolic and nuclear calcium signaling in atrial myocytes: IP3-mediated calcium release and the role of mitochondria," *Channels* (*Austin*) 2015, 9(3):129-138. However, increased forward-mode activity also leads to a positive net charge shift (1 $Ca^{2+}$ outwards, 3 Na+ inwards), which has been associated with an increased frequency of triggered, arrhythmic $Ca^{2+}$ release events in patients with AF. Voigt N, Li N, Wang Q, Wang W, Trafford A W, Abu-Taha I, Sun Q, Wieland T, Ravens U, Nattel S et al: "Enhanced sarcoplasmic reticulum $Ca^{2+}$ leak and increased $Na^+$-$Ca^{2+}$ exchanger function underlie delayed afterdepolarizations in patients with chronic atrial fibrillation," *Circulation* 2012, 125(17): 2059-2070. Recent data linked increased reverse mode NCX activity in ventricular cardiomyocytes to cardiac remodeling and diastolic dysfunction in a rat model of HFpEF (following partial nephrectomy). See, e.g., Primessnig U, Bracic T, Levijoki J, Otsomaa L, Pollesello P, Falcke M, Pieske B, Heinzel F R: "Long-term effects of Na(+)/Ca(2+) exchanger inhibition with ORM-11035 improves cardiac function and remodeling without lowering blood pressure in a model of heart failure with preserved ejection fraction," *Eur J Heart Fail* 2019, 21(12):1543-1552. In contrast, in atrial cardiomyocytes, increased forward mode NCX was a potential contributor to the amelioration of structural remodeling (e.g., LA enlargement) observed in this study. Interestingly, increased forward mode NCX activity after chronic treatment with sotagliflozin only occurs in HFpEF, but not WT. Even though intracellular $[Na^+]$ was not determined in the current study, a probable driver might be a reduction of (initially elevated) cytosolic $[Na^+]$. Different mechanisms of $[Na^+]$ lowering seem plausible: SGLT-2 inhibitors have been demonstrated to inhibit the $Na^+/H^+$ exchanger in murine cardiomyocytes. Uthman L, Baartscheer A, Bleijlevens B, Schumacher C A, Fiolet J W T, Koeman A, Jancev M, Hollmann M W, Weber N C, Coronel R et al: "Class effects of SGLT2 inhibitors in mouse cardiomyocytes and hearts: inhibition of Na(+)/H(+) exchanger, lowering of cytosolic Na(+) and vasodilation," Diabetologia 2018, 61(3):722-726. Indeed, our results confirm not only the debated presence of SGLT-2 in the LA but also support the notion of altered cytosolic $[Na^+]$ and $[Ca^{2+}]$ by its inhibition. Work by Lambert et al. indicates a contribution of the SGLT-1 transporter to cytosolic $[Na^+]$ in failing hearts, in particular in the presence of metabolic dysfunction (T2DM, obesity), making it another plausible site-of-action. Lambert R, Srodulski S, Peng X, Margulies K B, Despa F, Despa S: "Intracellular Na+ Concentration ([Na+]) Is Elevated in Diabetic Hearts Due to Enhanced $Na^+$-Glucose Cotransport," *J Am Heart Assoc* 2015, 4(9):e002183.

Mitochondria sequester large amounts of $Ca^{2+}$, which is a crucial regulator of energy production, mitochondrial morphology and apoptosis. In the ZSF model of HFpEF, an elevated mitochondrial $[Ca^{2+}]$ of LV cardiomyocytes at rest has been associated with increased cytosolic $[Ca^{2+}]$, mitochondrial swelling and reduced mitochondrial respiration. Miranda-Silva D, Wust R C I, Conceicao G, Goncalves-Rodrigues P, Goncalves N, Goncalves A, Kuster D W D, Leite-Moreira A F, van der Velden J, de Sousa Beleza J M et al: "Disturbed cardiac mitochondrial and cytosolic calcium handling in a metabolic risk-related rat model of heart failure with preserved ejection fraction," *Acta Physiol* (*Oxf*) 2020, 228(3):e13378. In this study, SGLT1/2 inhibition normalized abnormal mitochondrial swelling of LA cardiomyocytes in HFpEF and enhanced mitochondrial $Ca^{2+}$ buffer capacity. See FIG. 5. This effect might be explained by a reduction of mitochondrial [$Ca^{2+}$] at rest through reduced cytosolic [Na+] or [$Ca^{2+}$]. Maack C, Cortassa S, Aon M A, Ganesan A N, Liu T, O'Rourke B: "Elevated cytosolic Na+ decreases mitochondrial $Ca^{2+}$ uptake during excitation-contraction coupling and impairs energetic adaptation in cardiac myocytes," *Circ Res* 2006, 99(2):172-182. Mitochondrial $Ca^{2+}$ uptake has been shown to contribute to the buffering of cytosolic $Ca^{2+}$ peaks in cardiomyocytes and pharmacologic enhancement of mitochondrial $Ca^{2+}$ uptake was associated with decreased SCaEs in catecholaminergic ventricular tachycardia models. Schweitzer M K, Wilting F, Sedej S, Dreizehnter L, Dupper N J, Tian Q, Moretti A, My I, Kwon O, Priori S G et al: "Suppression of Arrhythmia by Enhancing Mitochondrial Ca(2+) Uptake in Catecholaminergic Ventricular Tachycardia Models," *JACC Basic Transl Sci* 2017, 2(6):737-747. An increased mitochondrial $Ca^{2+}$ buffer capacity might therefore contribute to decreased SCaEs amplitudes. Mitochondrial swelling has been described as a consequence of [$Ca^{2+}$] overload, consecutively leading to an opening of the mitochondrial permeability transition pore, mitochondrial depolarization, ROS generation and ultimately apoptosis. Lemasters J J, Theruvath T P, Zhong Z, Nieminen A L: "Mitochondrial calcium and the permeability transition in cell death," *Biochimica et biophysica acta* 2009, 1787(11):1395-1401. ROS-dependent SCaEs and spatial aspects of mitochondrial depolarizations are established mediators of cellular arrhythmias. Brown D A, O'Rourke B: "Cardiac mitochondria and arrhythmias," *Cardiovasc Res* 2010, 88(2):241-249. However, no effect was observed with dual SGLT1/2 inhibition, indicating that altered NCX activity and $Ca^{2+}$ buffer related mechanisms are of greater relevance for the observed sotagliflozin-related reverse atrial remodelling.

Reduced cardiac energy reserve and metabolic disorders are hallmark features of severe HF. In addition, almost 50% of HFpEF patients suffer from T2DM and are at particular high risk for HF hospitalization. Lindman B R, Davila-Roman V G, Mann D L, McNulty S, Semigran M J, Lewis G D, de las Fuentes L, Joseph S M, Vader J, Hernandez A F et al: "Cardiovascular phenotype in HFpEF patients with or without diabetes: a RELAX trial ancillary study," *Journal of the American College of Cardiology* 2014, 64(6):541-549. SGLT inhibition and in particular sotagliflozin have been shown to provide beneficial effects on blood pressure and body weight in the setting of diabetes potentially through reduced glycogen accumulation and ROS production. Cefalo C M A, Cinti F, Moffa S, Impronta F, Sorice G P, Mezza T, Pontecorvi A, Giaccari A: "Sotagliflozin, the first dual SGLT inhibitor: current outlook and perspectives," *Cardiovasc Diabetol* 2019, 18(1):20; Tsimihodimos V, Filippas-Ntekouan S, Elisaf M: "SGLT1 inhibition: Pros and Cons," *Eur J Pharmacol* 2018, 838:153-156. While dual SGLT inhibition has also been associated with an exacerbation of cardiac dysfunction following myocardial infarction (See Connelly K A, Zhang Y, Desjardins J F, Thai K, Gilbert R E: "Dual inhibition of sodium-glucose linked cotransporters 1 and 2 exacerbates cardiac dysfunction following experimental myocardial infarction," *Cardiovasc Diabetol* 2018, 17(1):99) in line with enhanced SGLT-1 mediated oxidative stress (See Li Z, Agrawal V, Ramratnam M, Sharma R K, D'Auria S, Sincoular A, Jakubiak M, Music M L, Kutschke W J, Huang X N et al: "Cardiac sodium-dependent glucose cotransporter 1 is a novel mediator of ischaemia/reperfusion injury," *Cardiovasc Res* 2019, 115 (11):1646-1658), others reported a protective role of SGLT-1 during the acute phase of ischemia/reperfusion injury. Yoshii A, Nagoshi T, Kashiwagi Y, Kimura H, Tanaka Y, Oi Y, Ito K, Yoshino T, Tanaka T D, Yoshimura M: "Cardiac ischemia-reperfusion injury under insulin-resistant conditions: SGLT1 but not SGLT2 plays a compensatory protective role in diet-induced obesity," *Cardiovasc Diabetol* 2019, 18(1): 85. Cardiac hypertrophy, a common predecessor of HFpEF, has frequently been linked to an increased glycolytic and decreased mitochondrial capacity. See, e.g., Leong H S, Grist M, Parsons H, Wambolt R B, Lopaschuk G D, Brownsey R, Allard M F: "Accelerated rates of glycolysis in the hypertrophied heart: are they a methodological artifact?" *Am J Physiol Endocrinol Metab* 2002, 282(5):E1039-1045. Recent animal studies suggest an additional uncoupling of glycolysis from mitochondrial glucose oxidation in HFpEF. Fillmore N, Levasseur J L, Fukushima A, Wagg C S, Wang W, Dyck J R B, Lopaschuk G D: "Uncoupling of glycolysis from glucose oxidation accompanies the development of heart failure with preserved ejection fraction," *Mol Med* 2018, 24(1):3. Work by Yoshii et al. has shown the significant role of SGLT-1 in the myocardial glucose uptake of the diabetic heart with respect to other glucose transporters (GLUT4 and GLUT1) (Yoshii, supra) and altered (mitochondrial) $Ca^{2+}$ homoeostasis is an established regulator of cellular energetics. Kohlhaas M, Nickel A G, Maack C: "Mitochondrial energetics and calcium coupling in the heart," *J Physiol* 2017, 595(12):3753-3763. Moreover, empagliflozin has been shown to mitigate diabetes related atrial fibrillation via improved mitochondrial function. Shao Q, Meng L, Lee S, Tse G, Gong M, Zhang Z, Zhao J, Zhao Y, Li G, Liu T: "Empagliflozin, a sodium glucose co-transporter-2 inhibitor, alleviates atrial remodeling and improves mitochondrial function in high-fat diet/streptozotocin-induced diabetic rats," *Cardiovasc Diabetol* 2019, 18(1):165. However, until this work it was unknown whether sotagliflozin would normalize glucose-mediated metabolic abnormalities related to cellular arrhythmogenesis of LA cardiomyocytes in HFpEF (e.g., $Ca^{2+}$ cycling, ROS production). This research shows that sotagliflozin prevents cytosolic $Ca^{2+}$ accumulation upon glucose influx and glycolytic inhibition in HFpEF and lowers ROS production during glucose starvation. Interestingly, ROS production normalized upon reintroduction of glucose only in HFpEF, indicating an increased glucose-dependency to meet cellular energetic demand while maintaining an adequate degree of pro-arrhythmogenic ROS production.

In conclusion, the dual SGLT1/2 inhibitor sotagliflozin ameliorates LA remodeling in HFpEF and exerts an anti-arrhythmic effect on LA cardiomyocytes.

All publications (e.g., patents and patent applications) cited above are incorporated herein by reference in their entireties.

The invention claimed is:

1. A method of treating atrial cardiomyopathy, which comprises administering to a patient in need thereof a therapeutically effective amount of sotagliflozin.

2. The method of claim 1, wherein the patient is suffering from heart failure.

3. The method of claim 1, wherein the sotagliflozin is administered orally.

4. The method of claim 3, wherein the therapeutically effective amount is at least 200 mg per day.

* * * * *